United States Patent [19]
Underwood et al.

[11] Patent Number: 6,160,406
[45] Date of Patent: Dec. 12, 2000

[54] CONDOM TESTING APPARATUS

[75] Inventors: Daniel S. Underwood; Barry W. Bass, both of Albany, Ga.

[73] Assignee: Agri Dynamics, Inc., Albany, Ga.

[21] Appl. No.: 09/226,753

[22] Filed: Jan. 6, 1999

Related U.S. Application Data

[60] Provisional application No. 60/105,672, Oct. 26, 1998.
[51] Int. Cl.[7] .................................................. G01N 27/00
[52] U.S. Cl. ......................... 324/558; 324/559; 324/517
[58] Field of Search .............................. 73/159; 324/558, 324/557, 559, 517

[56] References Cited

U.S. PATENT DOCUMENTS

| | | | |
|---|---|---|---|
| 2,221,323 | 11/1940 | Gammeter | 324/558 |
| 2,609,094 | 9/1952 | Fry | 324/558 |
| 2,649,960 | 8/1953 | Gammeter | 324/558 |
| 3,792,458 | 2/1974 | Smith | 324/558 |

Primary Examiner—Safet Metjahic
Assistant Examiner—Jose M. Solis
Attorney, Agent, or Firm—Thomas C. Saitta

[57] ABSTRACT

A condom testing apparatus utilizing an arcing electrical current to detect holes and excessively thin wall areas in a condom mounted on a conductive testing mandrel, where the condom is passed across a conductive fabric member to test the main body and transition portion of the condom, and is passed through the bristles of a conductive brush member to test the nipple end of the condom. In alternative embodiments, the apparatus may utilize only conductive fabric or only conductive brushes.

13 Claims, 3 Drawing Sheets

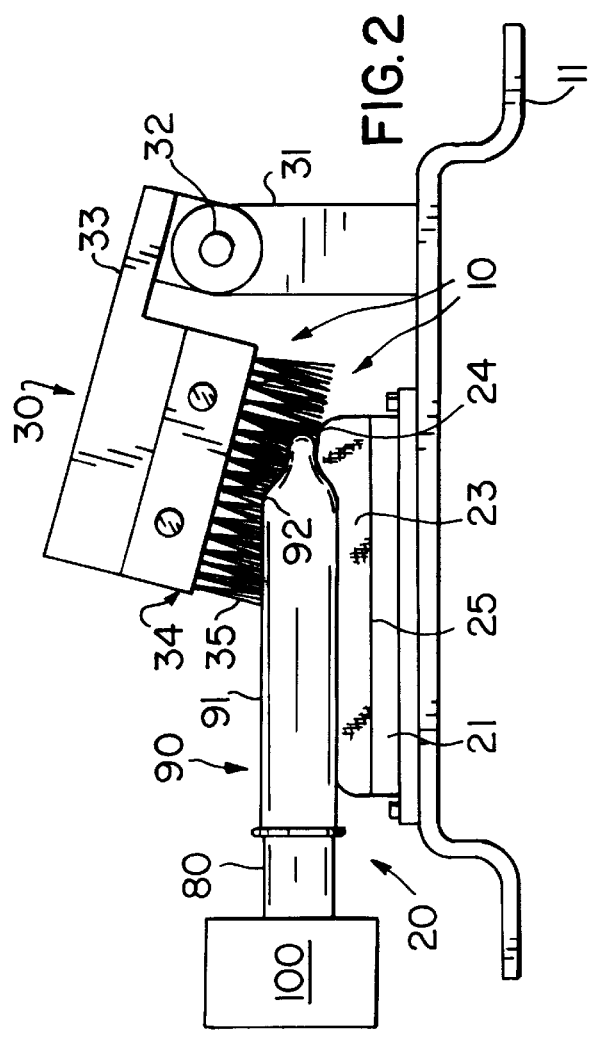
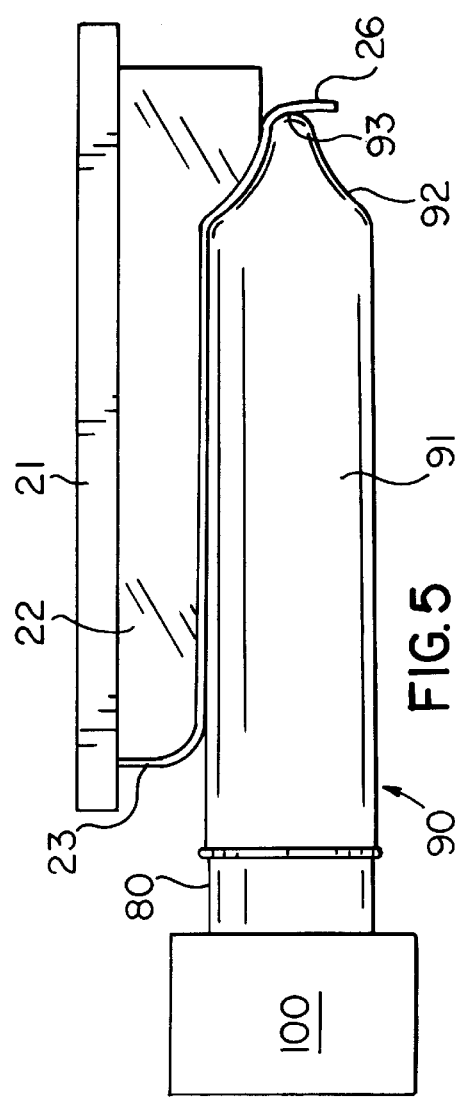

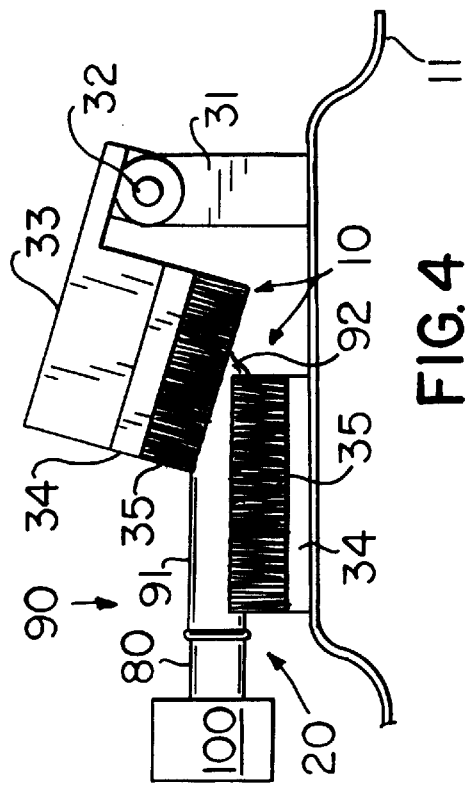
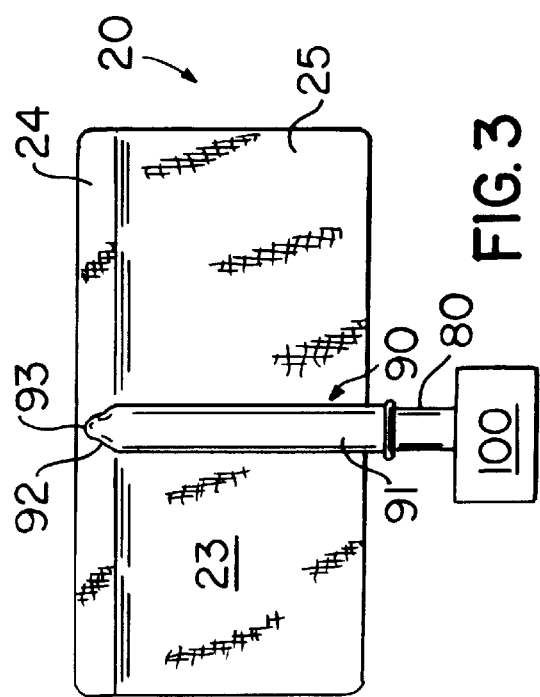

CONDOM TESTING APPARATUS

This application claims the benefit of the U.S. provisional application filed Oct. 26, 1998, and assigned serial No. 60/105,672.

BACKGROUND OF THE INVENTION

The invention relates generally to the field of condom testing equipment, and more particularly to such equipment which utilizes an electric arc to identify defective condoms.

By virtue of their intended use, it is absolutely essential that condoms provide a complete and impermeable barrier. Minute holes undetectable under visual inspection and excessively thin spots in the condom wall likely to fail in use are unacceptable. Because the manufacturing process produces huge numbers of condoms at a high rate and because the material of construction is purposely very thin and elastic, there is always likely to be a relatively small number of defective products in any production run. Because of this, every condom must be tested prior to packaging and distribution for sale to insure that no defective condoms are supplied to consumers.

One technique for testing a condom involves placing the condom on an electrically conductive mandrel, immersing the condom in water containing an electrical lead and then attempting to pass a current through the water to the mandrel. The condom material acts as an insulating barrier between the water and the mandrel to prevent completion of the electrical circuit, but any hole in the condom will allow the circuit to be completed, indicating that the condom is defective. Advantages of this technique are that low electrical voltages are required and the use of water as a conductive medium provides full contact to all portions of the condom. The major drawback to this technique is that the condoms must be dried prior to packaging. Another drawback is that the technique does not provide an indication of excessively thin spots in the condom wall which may tear in use, since the thin material is still sufficient to prevent passage of current from the water to the mandrel. A second known testing technique is to replace the conductive water with a conductive mesh material, the mesh being constructed so as to be very non-rigid so that it closely drapes against the condom on the conductive mandrel. The mandrel and condom are rotated while contacting the electrified mesh, and again any defects will allow the current to pass through the condom to the mandrel. A problem with this technique is that because the mesh must have a large amount of open area to achieve the desired flexibility, direct contact against every portion of the condom is not achieved, so a relatively high and thus dangerous amount of electrical current must be used—typically greater than 50 watts—to try to insure that the current will arc from the mandrel through a defect to the nearest piece of mesh. The variation in distance from the condom to particular points on the mesh as the condom is moved past the mesh also makes proper calibration of the electrical current difficult. Another problem is caused by the nipple portion of the condom. Because of this change in configuration from the generally cylindrical main body portion of the condom, providing enough contact between the mesh and the nipple material is problematic and defects can be missed.

It is an object of this invention to provide a highly efficient and accurate condom testing apparatus which overcomes the problems in the current testing equipment by providing for full contact over every portion of the condom, including the nipple area, so that an electric current can be used to detect any and every defect in the condom, including a defect consisting of an excessively thin wall portion which may fail during use, without requiring excessive preparation or post-testing steps in the testing process. These objects, as well as other objects which will be apparent from the description to follow, are accomplished preferably by providing an apparatus having an electrically conducting sheet fabric member for contacting the generally cylindrical portion of the condom on the mandrel and an electrically conducting brush member for contacting the nipple portion of the condom on the mandrel, or alternatively by providing an apparatus utilizing one or more flexible conducting sheet members only for contacting the full extent of the condom, or again alternatively by providing an apparatus utilizing one or more conductive brush members only for contacting the full extent of the condom.

SUMMARY OF THE INVENTION

In general the invention comprises a condom testing apparatus which has means to transport a condom loaded onto an electrically conductive testing mandrel through electrically conductive condom contacting means, with the mandrel and condom contacting means connected in a gapped electrical circuit such that the condom acts as an electrical insulator to prevent completion of the circuit, but where the electrical current will arc between or through any defect in the condom, such as a hole or excessively thin area in the condom wall, to complete the circuit, thus indicating that the condom is defective. The mandrel is shaped to correspond to the condom shape, including the nipple portion. The condom contacting means preferably comprises an electrically conductive fabric member and an electrically conductive brush member, but may also comprise only fabric members or only brush members. For the combination fabric and brush assembly, the fabric member is positioned to contact the generally cylindrical main body portion of the contact as it is brought across the fabric member. Preferably the fabric is backed by compressible padding such that the condom and mandrel, which is constructed to rotate freely during this testing stage, is rotated by frictional contact with the fabric member as it is moved through the condom contacting means. The fabric member is sufficiently long such that the condom is tested over 360 degrees, and preferably is provided excessively long such that more than one revolution of the condom is achieved during the test. The fabric member and pad is preferably constructed with a raised shoulder along the end corresponding to the nipple portion of the condom, so that the shoulder between the main body and the nipple, as well as the major portion of the nipple having a generally cylindrical configuration, are contacted. The fabric member is not positioned to contact the far end of the nipple portion, as the friction from the rotational movement would twist and damage the condom. The brush member is positioned along the nipple portion, preferably at an angle to the central axis of the rotating mandrel, in order to contact the extreme end of the nipple portion. In this manner every point of the condom is in direct contact with either the conductive fabric member or the conductive brush member, such that the electrical current will complete the circuit through any minute hole in the condom to indicate a defective condom. Furthermore, because the contact between the condom and both the fabric member and brush member is so extensive, and because the fabric member and brush member are positioned relatively close to the mandrel and at a relatively constant distance, the current strength can be adjusted such that the circuit will be completed even through excessively thin-walled areas of the condom, thus indicating a defective condom even where a hole is not present initially.

Alternatively, the fabric member may be omitted and the condom contacting means formed entirely of one or more conductive brush members appropriately arranged to contact the full extent of the exposed condom on the mandrel. In this construction means, such as a geared or friction mechanism, are provided to rotate the mandrel as it is passed across the brush member, since the coefficient of friction between the brush members and the mandrel would be insufficient to rotate the mandrel unaided. Another alternative construction utilizes a single or combination of conductive sheet members only, where preferably a sheet member is provided on the pad structure discussed above to provide friction to rotate the mandrel, the pad member being mounted above the mandrel, with a portion of the sheet member relatively loosely draped over the condom to contact the nipple end of the condom. The portion of the conductive sheet member contacting the nipple end is not affixed to any backing member, such that only a minimal amount of friction is created, thus insuring that the nipple end is not damaged during the rotation.

BRIEF DESCRIPTION OF THE DRAWINGS

FIG. 2 is a side view of the invention comprising the combination of conductive sheet member and conductive brush member, with a portion of the brush member removed to expose the mandrel and condom during the mid-portion of the testing operation.

FIG. 3 is a top view of the fabric member only of the invention comprising the combination of conductive sheet member and conductive brush member, with the brush member removed to show the mandrel and condom during the mid-portion of the testing operation.

FIG. 4 is a view of an alternative embodiment for the invention, where the condom contacting means comprises only conductive brush members.

FIG. 5 is a view of another alternative embodiment of the invention, where the condom contacting means comprises only a conductive sheet member.

DETAILED DESCRIPTION OF THE INVENTION

Figure 1:
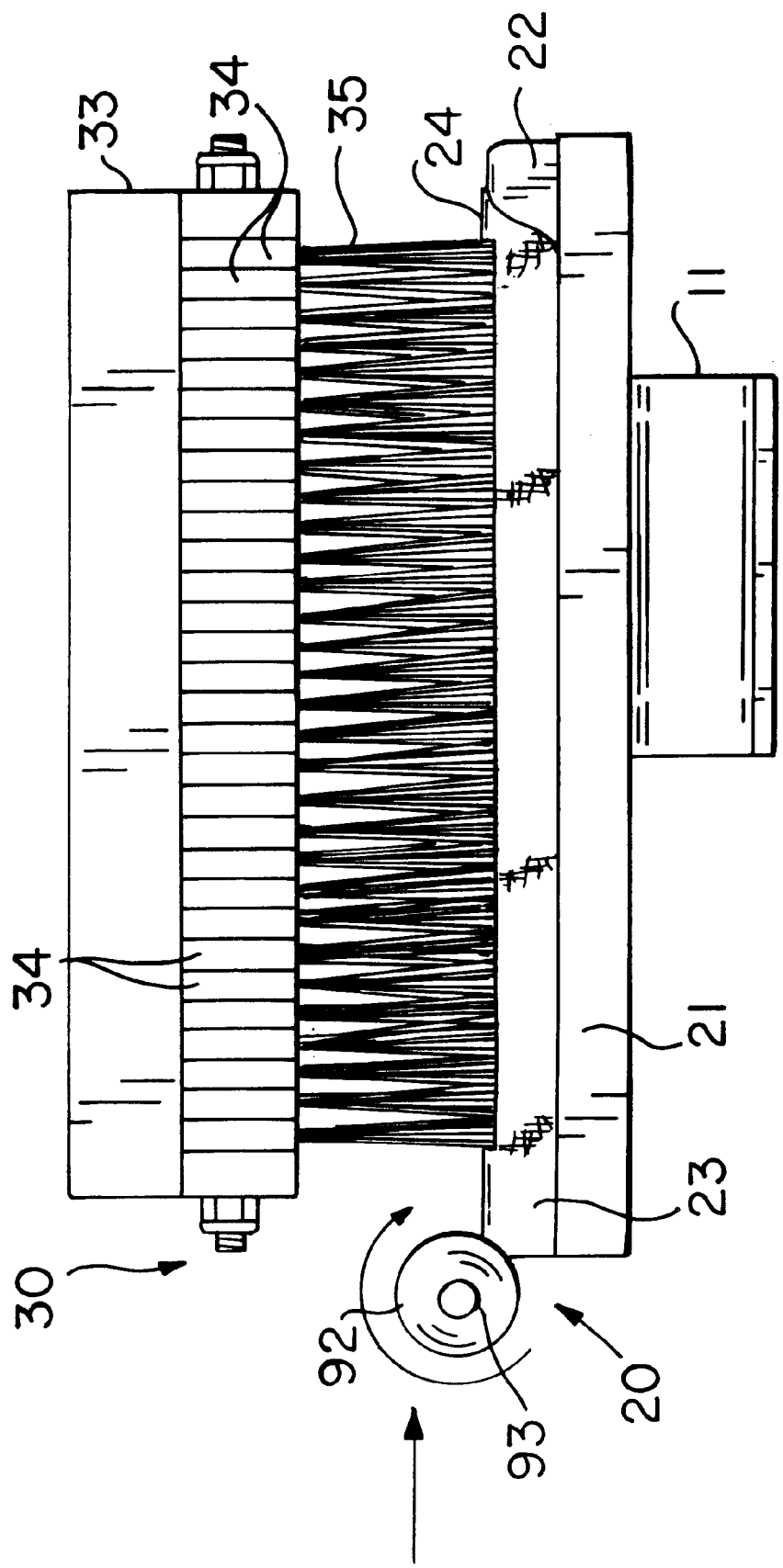
FIG. 1 is an end view of the invention comprising the combination of conductive sheet member and conductive brush member, showing the nipple end of the mandrel and condom as it initially contacts the condom contacting means.

With reference to the drawings, the invention will now be described in detail with regard for the best mode and the preferred embodiment. In general, the invention is an apparatus for testing condoms for defects, including holes and excessively thin wall areas, prior to packaging and distribution. The apparatus is preferably part of condom handling equipment having a mandrel to receive a condom in the unrolled condition, means to apply the condom to the mandrel prior to testing and means to remove the condom from the mandrel after testing, whether manually or mechanically, and means to transport the loaded mandrel through the condom testing apparatus as described. Such condom handling equipment is well known in the industry, and a representative example may be seen in U.S. Pat. No. 5,499,898 issued to Vonier et al., whose disclosure is incorporated herein by reference for purposes of illustrating such a condom testing apparatus where loaded mandrels are moved past and through various stations. The mandrels are connected to transport mechanisms which move the mandrel laterally relative to the longitudinal axis, with the mandrels being fixed, rotatable by power means or freely rotatable dependent on the particular individual operation required to be performed.

A condom 90 is composed of a thin, elastic material, typically a latex rubber, and is configured to have a generally cylindrical or tubular, open-ended, main body portion 91, a transition portion 92 where the diameter of the condom 90 is reduced—rapidly at first, then minimally for a short distance along the longitudinal axis, and finally rapidly again—to form a closed nipple end 93. The condom 90 material of construction is an electrical insulator, in that an electrical current at a level below the insulating threshold will not pass through the condom wall. For packaging, the main body portion 91 of the condom 90 is rolled along the central axis toward the nipple end. The testing mandrel 80 consists of a generally cylindrical body which is shaped to correspond to the overall shape of the condom 90, having a generally cylindrical main body, a transition region and reduced diameter end. The mandrel 80 is composed of an electrically conductive material, preferably a metal, and is connected to an electrical circuit. The mandrel 80 is connected to a mandrel transport means (shown representatively as 100) capable of moving the mandrel 80 laterally through the condom contacting means 10 for testing, the transport means 100 being of any type suitable for a moving the mandrel 80 in the necessary direction. The mandrel 80 is connected to the transport means 100 in a manner which allows free or controlled rotation of the mandrel 80 about the central axis, such as may be accomplished using bearings or the like in known manner.

The mandrel 80 loaded with a condom 90 for testing is translated through or across the condom contacting means 10, as shown in FIGS. 1 and 2. Condom contacting means 10 comprises a condom body contacting means 20 and a condom nipple contacting means 30, where the condom body contacting means 20 contacts the main body portion 91 and the transition portion 92 of the condom 90 and where the condom nipple contacting means 30 contacts the nipple end 93 and preferably the transition portion 92 of the condom 90 as the condom 90 and mandrel 80 are transported laterally through the condom contacting means 10. The condom contacting means 10 is provided with a mounting means such as base plate 10 to secure the assembly in a fixed manner relative to the condom transport means 100.

The body contacting portion 20 of the condom contacting means 10 comprises an electrically conductive fabric or sheet material member 23, which is preferably a durable fabric with some flexibility and a generally smooth surface to reduce friction and wear, preferably mounted onto a compressible backing pad 22 made of a polymer foam or a rubber, with the combination connected to a pad mount plate 21 or connected directly to the base plate 11. A suitable fabric member 23, for example, is a conductive sheeting sold by Aldan Industries consisting of a double coated, electrically conductive polyurethane on filament nylon, or an electrically conductive butyl rubber on spun polyester, sold as item numbers JB159B22 and JC159B25, respectively. The fabric member 23 and backing pad 22 is generally rectangular in shape, sufficiently long so as to contact the majority of the condom main body portion 91 when it is transported across the body contacting means 20 and with a width at least as great as the outer circumference of the condom main body portion 91, such that a full rotation of the condom 90 on the mandrel 80 results in contact to the fabric member 23 over the full circumference of the condom 90. Preferably, the fabric member 23 is wide enough to provide for at least 2.5 revolutions of the condom main body portion 91 while in contact with the fabric member 23, thus reducing even further the minimal chance that a defect might be missed in the test.

As best seen in FIGS. 2 and 3, the backing pad 22 and fabric member 23 of the body contacting means 20 is configured to have a generally planar surface 25 extending across the majority of the surface which contacts the condom main body portion 91, and a raised shoulder portion 24 disposed at the end of the mandrel 80, where the raised shoulder portion 24 generally conforms to the shape of the mandrel 80 and condom 90 in the transition portion 92. With this shape, the fabric member 23 contacts both the condom main body 91 and the condom transition portion 92 as the condom 90 and mandrel 80 are transported through the condom contacting means 10.

The nipple contacting means 30 comprises one or a plurality of electrically conductive brushes 34 having relatively dense bristle members 35 for direct contact with the condom 90, and means to mount the brushes 34 which as shown comprises a mounting post 31 connected to base plate 11, a brush mounting plate 33 and preferably pivot means 32 to connect the mounting plate 33 to the mounting post 31 such that the angle of the brushes 34 relative to the fabric member 23 can be adjusted as required. The contacting bristles 35 must occupy an area having a width in the mandrel transport direction at least equal to the circumference of the condom main body portion 91, and preferably occupy a width equal in distance to twice the circumference, such that contact will be maintained over two revolutions of the condom 90 as it is transported through the condom contacting means 10. The area covered by the bristles 35 should extend lengthwise in the mandrel axial direction at least slightly beyond the condom nipple end 93 and at least slightly beyond the condom transition portion 92, although it is possible to be shorter in this direction. The bristle 35 may be of generally equal length so as to present a generally planar contact surface, or they may be contoured to correspond to the shape of the loaded condom 90. In order to maximize contact along the condom nipple end 93 during testing, the brushes 35 are preferably mounted at an angle such that the bristle 35 ends are generally parallel to a line tangent to the nipple end 93 and the junction of the main body 91 and transition portion 92. The bristles 35 must extend to and preferably slightly beyond the axis of the condom nipple end 93, as the primary responsibility of the bristles 35 is to test the condom nipple end 93 for defects. Bristles 35 are used in order to provide contacting members which create minimal friction against the nipple end 93, such that rotation of the condom 90 as it passes through the bristles 35 does not produce excessive friction resulting in twisting and damage to the condom nipple end 93. The brush member 35 may be formed as a single body or formed of multiple individual brushes 35 joined in series. A suitable brush 35 for this purpose is a brush made by the Mill-Rose Company composed of a conductive plastic block and conductive bristles sold under the brand name THUNDERON.

The mandrel 80, fabric member 23 and the electrically conductive bristles 35 of the testing brush 34 are connected in an electrical circuit of common type used in such testing equipment, which is not shown in the drawings, such that when a mandrel 80 is passed through the condom contacting means 10, the circuit will be completed except for the insulation provided by the condom 90. An operating voltage in the range of 800 to 1800 vDC and operating current in the range of 0.006 to 0.010 amps has been found suitable for testing purposes. In particular such parameters are desirable in that the apparatus will not only detect holes in the condom 90, but the power is sufficient to jump gaps of approximately 3/1000 inches even through the condom wall, meaning that the current will arc or burn through excessively thin areas in the condom material, thus indicating a defective condom 90 even where a hole is not present. When the current passes through a hole or an excessively thin area between the mandrel 80 and either the fabric member 23 or the bristles 35, the circuit is completed and the condom 90 is noted as defective in further handling.

As shown in FIG. 1, the electrically conductive fabric member 23 may extend slightly beyond both edges of the electrically conductive bristles 35 along the transport direction of the mandrel 80. With this construction, the mandrel 80 and condom 90 will first contact the fabric member 23, which is disposed such that the compressive pad 22 is slightly compressed so that sufficient friction occurs to cause the mandrel 80 to rotate as it is moved along the fabric member 23, which prevents the condom material being dragged across the surface of the fabric member 23. It is desirable that the fabric member 23 be contacted first, since in the instances where a condom 90 is not loaded onto the mandrel 80, the current will arc between the fabric member 23 and the mandrel 80 rather than between the mandrel 80 and the bristles 35, which deteriorates the ends of the bristles 35. It is preferred, however, to solve the arcing problem by the incorporation of appropriate circuitry. As the transport means 100 moves the mandrel 80 laterally through the condom contacting means 10, the condom 90 is rotated such that the entire circumference of the condom main body 91 and transition portion 92 contacts the fabric member 23, and such that the entire circumference and end of the condom nipple end 93 and the transition portion 92 contacts the bristles 35, such that every existing or potential defect in the condom 90 will be detected.

An alternative embodiment is illustrated in FIG. 4, in which the body contacting means 20 now comprises a second brush assembly 34 with electrically conductive bristles 35 which are positioned to contact the main body portion of the condom 90. The contract area of the bristles 35 is generally rectangular and at least as wide in the mandrel travel direction as the circumference of the condom main body 91 and sufficiently long to extend over the vast majority of the condom main body 91. In another alternative version, a single brush member 34 may be provided with a sufficient number of bristles 35 properly positioned, contoured and angled to contact the main body portion 91, transition portion 92 and nipple end 93 of the condom 90. The brush or brush assemblies 34 are connected in gapped electrical circuitry with the conductive mandrel 80, such that a current will arc between any holes or excessively thin areas in the wall of the condom 90 to indicate a defective condom 90. Because the contact friction between the bristles 35 and the condom 90 is very minimal, the mandrel 80 must be actively rotated in order to expose every portion of the condom 90 to the bristles 35. This is easily accomplished in known manner to those skilled in the art by mechanical gearing or friction means.

Still another alternative embodiment for providing continuous contact with the condom 90 is shown in FIG. 5, which utilizes a conductive sheet fabric member 23, of the type previously set forth above. The major portion of the sheet member 23 is mounted as before onto a compressible backing pad 22 and pad mount plate 21, and the pad mount plate 21 is arranged in the apparatus so as to be positioned above the mandrel 80 and condom 90 as they pass through the testing area. The backing pad 22 is configured to define a generally planar surface 25 for contacting the cylindrical body portion 91 of the condom 90 and a shoulder portion 24 for contacting the transition or reduction portion 92 of the condom 90. The conductive sheet member 23 is affixed to the backing pad 22 over the planar surface 25 and shoulder portion 24. A portion of the sheet member 23 extending beyond the shoulder portion 24 is not attached to the backing pad 22. This free hanging, unmounted flap portion 26 is positioned adjacent and abutting the nipple end 93 of the condom 90, and extends a distance at least as great as the maximum circumference of the condom 90 along the direction of mandrel travel. The flap portion 26 is the nipple contacting means 30 for the testing apparatus in this embodiment. Because the flap portion 26 of the conductive sheet member 23 is not attached to the backing pad 22, contact friction between the flap portion 26 and the nipple end 93 is minimized, such that the nipple end 93 is not damaged as it is rotated and translated through the testing area. As before, the conductive sheet member 23 is part of a gapped electrical circuit such that any defects in the condom 90 result in an a closed circuit between the conductive sheet 23 and the conductive mandrel 80.

It is contemplated that equivalents and substitutions for certain elements and components set forth above may be obvious to those skilled in the art, and thus the true scope and definition of the invention is to be as set forth in the following claims.

We claim:

1. A condom testing apparatus for identifying defective condoms having holes or excessively thin wall areas by passage of an electrical current through such defect, the apparatus comprising:
    an electrically conductive mandrel to receive a condom having a cylindrical body portion, a transition portion and a nipple end, where said mandrel is connected to mandrel transport means to move said mandrel across condom contacting means;
    condom contacting means comprising condom body contacting means and condom nipple contacting means where said condom body contacting means comprises an electrically conductive, flexible sheet member and said condom nipple contacting means comprises an electrically conductive brush member having bristles adapted to contact at least said condom nipple, wherein said brush member extends in the direction of movement of said mandrel across said condom contacting means at least a distance equal to the circumference of said mandrel cylindrical body portion;
    where said mandrel and said condom contacting means are connected in a gapped electrical circuit such that an electric current passes through any defects in a condom mounted onto said mandrel to indicate that the condom is defective.

2. The apparatus of claim 1, where said condom body contacting means further comprises a compressible backing pad and said sheet member is affixed to said backing pad, where said mandrel rotates as said mandrel is moved across said sheet member of said condom contacting means.

3. The apparatus of claim 2, where said rotation is caused by frictional contact between said condom on said mandrel and said sheet member.

4. The apparatus of claim 2, where said backing pad has a raised shoulder corresponding to said transitional portion of said condom, whereby said transitional portion of said condom contacts said shoulder of said backing pad when said mandrel is moved across said sheet member of said condom contacting means.

5. The apparatus of claim 4, where said mandrel and said condom contact said sheet member before contacting said brush member.

6. A condom testing apparatus for identifying defective condoms having holes or excessively thin wall areas by passage of an electrical current through such defect, the apparatus comprising:
    an electrically conductive mandrel to receive a condom having a cylindrical body portion, a transition portion and a nipple end, where said mandrel is connected to mandrel transport means to move said mandrel across condom contacting means;
    condom contacting means comprising condom body contacting means and condom nipple contacting means where said condom body contacting means comprises an electrically conductive brush member having bristles adapted to contact at least said condom body and said condom nipple contacting means comprises an electrically conductive brush member having bristles adapted to contact at least said condom nipple;
    where said mandrel and said condom contacting means are connected in a gapped electrical circuit such that an electric current passes through any defects in a condom mounted onto said mandrel to indicate that the condom is defective.

7. The apparatus of claim 6, where said mandrel is rotated as it is moved across said condom contacting means.

8. A condom testing apparatus for identifying defective condoms having holes or excessively thin wall areas by passage of an electrical current through such defect, the apparatus comprising:
    an electrically conductive mandrel to receive a condom having a cylindrical body portion, a transition portion and a nipple end, where said mandrel is connected to mandrel transport means to move said mandrel across condom contacting means;
    condom contacting means comprising condom body contacting means and condom nipple contacting means where said condom body contacting means and said condom nipple contacting means comprise an electrically conductive, flexible sheet member;
    where said condom body contacting means further comprises a compressible backing pad and said sheet member is affixed to said backing pad, where said mandrel rotates as said mandrel is moved across said sheet member of said condom contacting means, and where said backing pad has a raised shoulder corresponding to said transitional portion of said condom, whereby said transitional portion of said condom contacts said shoulder of said backing pad when said mandrel is moved across said sheet member of said condom contacting means;
    where said sheet member is positioned above said mandrel and said nipple contacting portion comprises a flap portion of said sheet member which extends beyond said shoulder and is not affixed to said backing pad; and
    where said mandrel and said condom contacting means are connected in a gapped electrical circuit such that an electric current passes through any defects in a condom mounted onto said mandrel to indicate that the condom is defective.

9. The apparatus of claim 1, where said brush member extends in the direction of movement of said mandrel across said condom contacting means at least a distance equal to twice the circumference of said mandrel cylindrical body portion.

10. The apparatus of claim 6, where said brush members extend in the direction of movement of said mandrel across said condom contacting means at least a distance equal to the circumference of said mandrel cylindrical body portion.

11. The apparatus of claim 10, where said brush members extend in the direction of movement of said mandrel across said condom contacting means at least a distance equal to twice the circumference of said mandrel cylindrical body portion.

12. The apparatus of claim 6, where said brush member comprising said condom nipple contacting means is mounted at an angle relative to said mandrel.

13. The apparatus of claim 1, where said brush member is mounted at an angle relative to said mandrel.

* * * * *